(12) United States Patent
McCullough et al.

(10) Patent No.: US 11,551,814 B2
(45) Date of Patent: Jan. 10, 2023

(54) PREDICTING RISK FOR PREVENTABLE PATIENT HEALTHCARE EVENTS

(71) Applicant: 3M INNOVATIVE PROPERTIES COMPANY, St. Paul, MN (US)

(72) Inventors: Elizabeth C. McCullough, Silver Spring, MD (US); Richard L. Fuller, Pasadena, MD (US); Norbert I. Goldfield, Northampton, MA (US); Richard F. Averill, Seymour, CT (US)

(73) Assignee: 3M Innovative Properties Company, St. Paul, MN (US)

( * ) Notice: Subject to any disclaimer, the term of this patent is extended or adjusted under 35 U.S.C. 154(b) by 737 days.

(21) Appl. No.: 15/126,702

(22) PCT Filed: Mar. 16, 2015

(86) PCT No.: PCT/US2015/020680
§ 371 (c)(1),
(2) Date: Sep. 16, 2016

(87) PCT Pub. No.: WO2015/142709
PCT Pub. Date: Sep. 24, 2015

(65) Prior Publication Data
US 2017/0109492 A1  Apr. 20, 2017

Related U.S. Application Data

(60) Provisional application No. 61/954,010, filed on Mar. 17, 2014.

(51) Int. Cl.
*G16H 50/30* (2018.01)
*G16H 40/67* (2018.01)
*H04L 67/01* (2022.01)

(52) U.S. Cl.
CPC ............. *G16H 50/30* (2018.01); *G16H 40/67* (2018.01); *H04L 67/01* (2022.05)

(58) Field of Classification Search
CPC ..... G16H 50/30; G06F 19/324; G06F 19/328; G06F 19/3418; H04L 67/42
See application file for complete search history.

(56) References Cited

U.S. PATENT DOCUMENTS 7,127,407 B1   10/2006   Averill
8,190,451 B2   5/2012   Lloyd
(Continued)

FOREIGN PATENT DOCUMENTS

WO   WO 2014-134026   9/2014
WO   WO 2015-142708   9/2015

OTHER PUBLICATIONS

Amarasingham, "An Automated Model to Identify Heart Failure Patients at Risk for 30-Day Readmission or Death Using Electronic Medical Record Data", Medical Care, 2010, vol. 48, No. 11, pp. 981-988.
(Continued)

*Primary Examiner* — Michael Tomaszewski
*Assistant Examiner* — Mohmad Muqueeth
(74) *Attorney, Agent, or Firm* — Brian D. Bender (57) ABSTRACT

Evaluating future healthcare event risks of a patient includes receiving, at one or more computers, patient healthcare data for the patient, wherein the patient healthcare data represents a healthcare event and includes one or more healthcare codes, accessing, with the one or more computers, a database that associates the healthcare event and the healthcare codes with risks of potentially preventable healthcare events, and presenting, with the one or more computers, indications of the risks of potentially preventable healthcare
(Continued)

events to a user to facilitate mitigation of the risks of potentially preventable healthcare events for the patient.

20 Claims, 5 Drawing Sheets

(56) References Cited

U.S. PATENT DOCUMENTS

| | | | |
|---|---|---|---|
| 2003/0130973 A1* | 7/2003 | Sumner, II | G06F 19/3481 706/45 |
| 2009/0138285 A1 | 5/2009 | Denberg | |
| 2009/0307180 A1 | 12/2009 | Colby | |
| 2011/0295622 A1* | 12/2011 | Farooq | G16H 40/20 705/3 |
| 2011/0313788 A1* | 12/2011 | Amland | G16H 50/30 705/3 |
| 2012/0046965 A1 | 2/2012 | Ryan | |
| 2013/0191158 A1* | 7/2013 | Fillmore | G06F 19/00 705/3 |
| 2013/0290005 A1 | 10/2013 | Vesto | |
| 2014/0012592 A1 | 1/2014 | Ivanovic | |
| 2014/0025395 A1 | 1/2014 | Averill | |
| 2014/0278490 A1* | 9/2014 | Namazifar | G16H 50/30 705/2 |
| 2014/0278547 A1* | 9/2014 | Wickert | G06F 19/00 705/3 |

OTHER PUBLICATIONS

Donze, "Potentially Avoidable 30-Day Hospital Readmissions in Medical Patients", Journal of the American Medical Association Internal Medicine, 2013, pp. E1-E7.

Hansen, "Interventions to Reduce 30-Day Rehospitalization: A Systematic Review", Annals of Internal Medicine, 2011, vol. 155, No. 8, pp. 520-528.

Kansagara, "Risk Prediction Models for Hospital Readmission—A Systematic Review", Journal of the American Medical Association, 2011, vol. 306, No. 15, pp. 1688-1698.

International Search Report for PCT International Application No. PCT/US2015/20680, dated Jul. 1, 2015, 2 pages.

\* cited by examiner

FIG. 5

PREDICTING RISK FOR PREVENTABLE PATIENT HEALTHCARE EVENTS

CROSS REFERENCE TO RELATED APPLICATIONS

This application is a national stage filing under 35 U.S.C. 371 of PCT/US2015/020680, filed Mar. 16, 2015, which claims the benefit of U.S. Provisional Application No. 61/954,010, filed Mar. 17, 2014, the disclosure of which is incorporated by reference in its/their entirety herein.

TECHNICAL FIELD

This disclosure relates to analysis of medical data in the medical industry and more specifically analysis of patient medical data.

BACKGROUND

In the healthcare field, patient readmissions are a source of waste and contribute to increased overall costs for the system, which translate to higher payment costs for insurers and higher healthcare coverage of individuals. In addition, some major payers such as Medicare have begun to impose substantial payment penalties to hospitals that have high readmission rates. As a result, hospitals are making major investment in processes and programs to reduce patient readmission. In order to be most effective, efforts to reduce readmissions should begin and occur during a patient's stay in the hospital.

SUMMARY

In general, this disclosure relates to predicting risk for preventable patient healthcare events, such as patient readmission, on a patient-by-patient basis. In different examples, predicting risk for preventable patient healthcare events may be based on: a patient's reason for hospitalization, acuity, demographic characteristics, burden of chronic illness, health status, socioeconomic status, pharmaceutical usage, and/or detailed clinical data such as history and laboratory test results. The probability of the occurrence of specific types of potentially preventable readmissions may be used to allocate medical provider, such as hospital, resources during a patient's hospital stay in order to prevent post discharge readmissions. In addition, the probability of the occurrence of specific types of potentially preventable readmissions may be used to compare the performance of individual providers, including physicians, in terms of their rate of potentially preventable readmissions.

In one example, this disclosure is directed to a method of evaluating future healthcare event risks of a patient, via one or more computers. The method comprises receiving, at the one or more computers, patient healthcare data for the patient, wherein the patient healthcare data represents a healthcare event and includes one or more healthcare codes, accessing, with the one or more computers, a database that associates the healthcare event and the healthcare codes with risks of potentially preventable healthcare events, presenting, with the one or more computers, indications of the risks of potentially preventable healthcare events to a user to facilitate mitigation of the risks of potentially preventable healthcare events for the patient.

In another example, this disclosure is directed to a computer-readable storage medium that stores computer-executable instructions that, when executed, configure a processor to access patient healthcare data for a patient, wherein the patient healthcare data represents a healthcare event and includes one or more healthcare codes, access a database that associates the healthcare event and the healthcare codes with risks of potentially preventable healthcare events, and present indications of the risks of potentially preventable healthcare events to a user to facilitate mitigation of the risks of potentially preventable healthcare events for the patient.

In a further example, this disclosure is directed to a computer system comprising one or more databases storing patient healthcare data for a patient and associations between healthcare codes and risks of potentially preventable healthcare events, and one or more processors. The one or more processors being configured to access the patient healthcare data for the patient, wherein the patient healthcare data represents a healthcare event and includes one or more healthcare codes, access associations between the healthcare event and the healthcare codes with risks of potentially preventable healthcare events, and present indications of the risks of potentially preventable healthcare events to a user to facilitate mitigation of the risks of potentially preventable healthcare events for the patient.

In an example, this disclosure is directed to a method of evaluating future readmission risks of a patient, via one or more computers, the method comprising receiving, at the one or more computers, patient healthcare data for the patient, wherein the patient healthcare data represents a healthcare event associated with a hospital admission and includes one or more healthcare codes, accessing, with the one or more computers, a database that associates the healthcare codes with risks of potentially preventable readmission events, and presenting, with the one or more computers, indications of the risks of potentially preventable readmission events to a user to facilitate mitigation of the risks of potentially preventable readmission events for the patient.

In another example, this disclosure is directed to a method of evaluating future healthcare event risks of a patient, via one or more computers. The method comprises accessing, with the one or more computers, indications of risks of potentially preventable healthcare events associated with the patient, accessing, with the one or more computers, personal health information associated with the patient, adjusting, with the one or more computers, the risks of potentially preventable healthcare events associated with the patient based on the personal health information associated with the patient, produce adjusted risks of potentially preventable healthcare events, and presenting, with the one or more computers, indications of the adjusted risks of potentially preventable healthcare events to a user to facilitate mitigation of the risks of potentially preventable healthcare events for the patient.

In a further example, this disclosure is directed to a computer-readable storage medium that stores computer-executable instructions that, when executed, configure a processor to access indications of risks of potentially preventable healthcare events associated with the patient, access personal health information associated with the patient, adjust the risks of potentially preventable healthcare events associated with the patient based on the personal health information associated with the patient, produce adjusted risks of potentially preventable healthcare events, and present indications of the adjusted risks of potentially preventable healthcare events to a user to facilitate mitigation of the risks of potentially preventable healthcare events for the patient.

In another example, this disclosure is directed to a computer system comprising one or more databases storing indications of risks of potentially preventable healthcare events associated with the patient and personal health information associated with the patient, and one or more processors. The one or more processors being configured to access the indications of risks of potentially preventable healthcare events associated with the patient, accessing the personal health information associated with the patient, adjust the risks of potentially preventable healthcare events associated with the patient based on the personal health information associated with the patient, produce adjusted risks of potentially preventable healthcare events, and present indications of the adjusted risks of potentially preventable healthcare events to a user to facilitate mitigation of the risks of potentially preventable healthcare events for the patient.

The details of one or more examples of this disclosure are set forth in the accompanying drawings and the description below. Other features, objects, and advantages of this disclosure will be apparent from the description and drawings, and from the claims.

DETAILED DESCRIPTION

This disclosure describes systems and techniques for determining risks of potentially preventable healthcare events. The systems and techniques may be used by a healthcare provider, such as a hospital or health maintenance organization, to efficiently allocate resources to mitigate risks of identified potentially preventable healthcare events on a patient-by-patient basis. For example, healthcare providers may receive indications of the risks of specific potentially preventable healthcare events for admitted patients in time to mitigate the identified risks. Generally, such patient-by-patient risk analysis is completed and disseminated prior to the discharge of a patient from a medical facility as it usually most effective to mitigate identified risks before the patient is discharged from the medical facility. In other examples, patient-by-patient risk analysis may be completed at discharge or immediately following discharge and still allow mitigation of risks of the identified potentially preventable healthcare events associated with particular patients.

Although the techniques disclosed herein are generally directed to predicting potentially preventable readmissions, the techniques are equally applicable to preventing other potentially preventable healthcare events. As referred to herein, healthcare events include inpatient admissions, emergency room visits, and outpatient ancillary services.

While the described techniques may clearly be used to improve patient care, there are also financial incentives for healthcare providers to reduce preventable patient readmissions. For example, some major payers such as Medicare have begun to impose substantial payment penalties to medical providers, such as hospitals, that have high readmission rates. Interventions to reduce patient readmissions are labor intensive and medical providers have limited staff to devote to readmission reduction efforts. The disclosed techniques facilitate efficient targeting readmission prevention efforts on those patients who are most likely to be readmitted, and for whom the readmission prevention efforts are most likely to be successful.

As one example, the disclosed techniques allow medical providers to predict at any point during an inpatient stay the likelihood (probability) that the patient will have a potentially preventable readmission. Research suggests that roughly forty percent of patient readmissions are not preventable. For example, a readmission due to an injury from a traffic accident or appendicitis would not be preventable if that patient's prior admission was factually unrelated to the traffic accident or appendicitis.

The techniques disclosed herein focus on predicting risk of readmissions that are potentially preventable because these are the only readmissions for which an intervention can be successful. Once the probability (or risk) of a preventable readmission is known for an individual patient, medical providers, such as hospitals, can use the probability to prioritize the deployment of their limited readmission intervention resources to those patients with the highest risk of having a potentially preventable readmission. The probability of potentially preventable readmissions can also be used to compute the expected number of potentially preventable readmissions for individual providers including physicians. The expected number of potentially preventable readmissions for a provider can then be compared to the actual number of potentially preventable readmissions that occurred for that provider. By comparing the actual and expected number of potentially preventable readmissions, education, interventions and payment penalties can be targeted to providers with poor potentially preventable readmission performance.

In addition to predicting the risk of potentially preventable healthcare events in the future for individual patients, the presently described system and techniques may also classify current or past individual healthcare events as either potentially preventable or not-potentially preventable. Potentially preventable healthcare events are those events that may represent excessive healthcare services, i.e. waste. Healthcare providers may wish to determine and track their rate of potentially preventable healthcare events in order to implement internal procedures to reduce the rate.

As described in greater detail below, the methods of this disclosure may be performed by one or more computers. As examples, the methods may be performed by a standalone computer, or may be executed in a client-server environment in which a user views the determined risks of potentially preventable healthcare events at a client computer. In the latter case, the client computer may communicate with a server computer. The server computer may store the patient healthcare data and apply the techniques of this disclosure to determine risks of potentially preventable healthcare events and output the results to the client computer. In addition to these two examples, the methods may be performed in other computer environments.

In one example, a method includes receiving, at the one or more computers, patient healthcare data, wherein the patient healthcare data represents a healthcare event and includes one or more healthcare codes. The method may further include determining, by the one or more computers and based on the one or more healthcare codes, one or more patient factors associated with the healthcare event. After determining the one or more patient factors, the method may determine, by the one or more computers and based on the one or more healthcare codes and the one or more patient factors associated with the healthcare event, risks of potentially preventable healthcare events. In some examples, the healthcare event may comprise one of an inpatient admission, an emergency room visit, and an outpatient ancillary service.

Throughout the description of the techniques and systems of the present disclosure, the description exemplifies the techniques and systems as determining risks of potentially preventable healthcare events. In the context of this description, the term potentially preventable healthcare event implies a healthcare event is associated with one or more healthcare codes and/or determined patient factors that are consistent with a potentially preventable event. In other words, the techniques and systems described herein focus only on determining risk of potentially preventable healthcare events, and not on the overall risks of healthcare events. In some particular examples, the techniques and systems described herein focus may be specifically directed to determining risks of potentially preventable readmissions. In further more specific examples, such techniques may be applied to determining risks of potentially preventable hospital readmissions only or risks of potentially preventable hospital readmissions, emergency room (ER) stays and outpatient observation stays.

Figure 1:
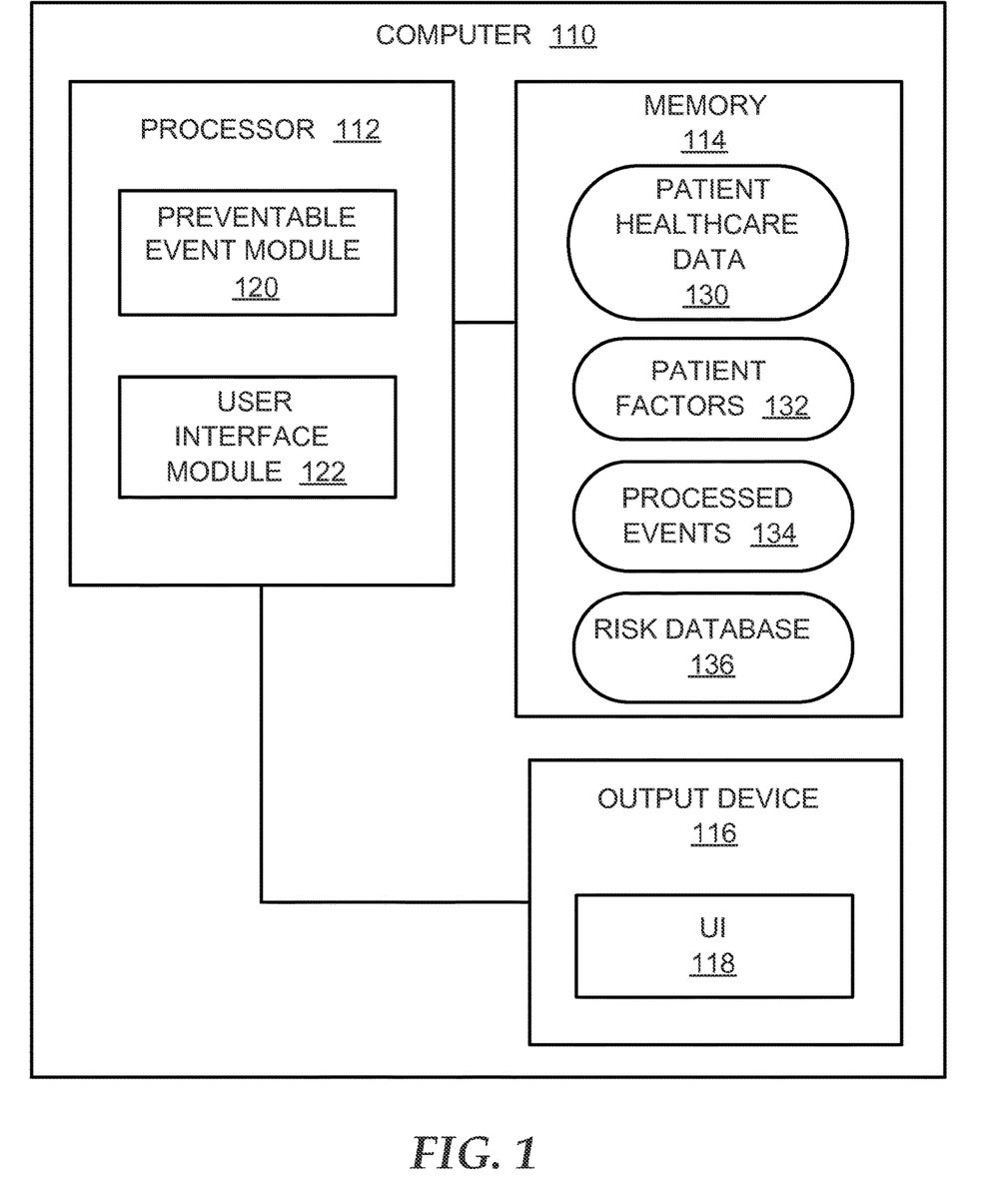
FIG. 1 is a block diagram illustrating an example of a standalone computer system for determining risks of potentially preventable healthcare events.

FIG. 1 is a block diagram illustrating an example of a stand-alone computerized system for determining risks of potentially preventable healthcare events consistent with this disclosure. The system comprises computer 110 that includes a processor 112, a memory 114, and an output device 116, such as a display screen. Computer 110 may also include many other components, and the functions of any of the illustrated components including computer 110, processor 112, a memory 114, and output device 216, may be distributed across multiple components and separate computing devices, e.g., as illustrated with respect to the distributed computing system of FIG. 2. The illustrated components are shown merely to explain various aspects of this disclosure.

Memory 114 includes patient healthcare data 130, which may comprise data collected in documents such as patient healthcare records, among other information. Memory 114 further includes risk database 136. Risk database 136 associates healthcare events and healthcare codes with risks of potentially preventable healthcare events. In some examples, risk database 136 includes a matrix or list that identifies potentially preventable healthcare events for each of a plurality of healthcare codes. Memory 114 may further include patient factors 132 and processed events 134. Processor 112 is configured to include a user interface module 122 and a preventable event module 120 that executes techniques of this disclosure with respect to patient healthcare data 130 and, in some cases, patient factors 132. In some examples, processed events 134 may comprise information such as which healthcare events processor 112 and/or preventable event module 120 determines to be potentially preventable healthcare events associated with a current healthcare event or code of a patient. Also in some examples, patient factors 132 may store various associations, as described below, between one or more healthcare codes.

Processor 112 may comprise a general-purpose microprocessor, a specially designed processor, an application specific integrated circuit (ASIC), a field programmable gate array (FPGA), a collection of discrete logic, or any type of processing device capable of executing the techniques described herein. In one example, memory 114 may store program instructions (e.g., software instructions) that are executed by processor 112 to carry out the techniques described herein. In other examples, the techniques may be executed by specifically programmed circuitry of processor 112. In these or other ways, processor 112 may be configured to execute the techniques described herein.

Memory 114 may represent any volatile or non-volatile storage elements. Examples include random access memory (RAM) such as synchronous dynamic random access memory (SDRAM), read-only memory (ROM), non-volatile random access memory (NVRAM), electrically erasable programmable read-only memory (EEPROM), and FLASH memory. Examples may also include non-volatile storage, such as a hard-disk, magnetic tape, a magnetic or optical data storage media, a compact disk (CD), a digital versatile disk (DVD), a Blu-ray disk, and a holographic data storage media.

Output device 116 may comprise a display screen, although this disclosure is not necessarily limited in this respect, and may also include other types of output capabilities. In some cases, output device 116 may generally represent both a display screen and a printer in some cases. Preventable event module 120, and in some cases in conjunction with user interface module 122, may be configured to cause output device 116 to output patient healthcare data 130, patient factors 132, processed events 134, or other data. In some instances, output device 116 may include a user interface (UI) 118. UI 118 may comprise an easily readable interface for displaying the output information.

In one example, preventable event module 120 receives patient healthcare data 130. Generally, patient healthcare data 130 may include information included in a patient healthcare record or any other documents or files describing patient healthcare events. For example, when a patient has an encounter with a healthcare facility, such as during an inpatient admission, an emergency room visit, or an outpatient visit, all of the information gathered during the encounter and preceding the encounter may be consolidated into a patient healthcare record describing the particular healthcare event. In one example, such a patient healthcare record may include any procedures performed, any medications prescribed, any notes written by a physician or nurse, and generally any other information concerning the healthcare event. Additionally, the information may include the location of residence of the patient. For example, the location of residence may indicate whether the patient currently resides in a private home or in a managed home, such as a nursing home or other permanent or semi-permanent medical facility.

Patient healthcare data 130 may further include information from healthcare claims forms. These claims forms, or other documents in the patient medical record, may include one or more standard healthcare codes, as described in more detail below. The documents referred to herein are not limited to paper documents physically placed in a folder or other record keeping device. Increasingly, medical records are stored electronically. Accordingly, patient healthcare data 130 may be paper records fed into computer 110, or computer 110 may receive patient healthcare data electronically. Additionally, each piece of information included in patient data 130 may further be associated with a particular date. For example, patient healthcare data 130 may include multiple pieces of information associated with an inpatient admission event occurring on Mar. 20, 2005. In such an example, each piece of information related to that inpatient admission event may further be associated with the date Mar. 20, 2005 (or other relevant date if all the services or procedures relating to the inpatient admission did not occur on that exact date). In total, patient healthcare data 130 may comprise a complete or partial medical history. For example, all of the healthcare events for a given patient may be placed in order by date, thereby giving an overview of the chronological healthcare events that have occurred for a given patient.

Patient healthcare data 130 may further include one or more standard healthcare codes. In some examples, the patient healthcare records or the healthcare claims forms may include one or more of these standard healthcare codes, which generally may describe the services and procedures delivered to a patient. Examples of such healthcare codes include codes associated with the International Classification of Diseases (ICD) codes, Current Procedural Technology (CPT) codes, Healthcare Common Procedural Coding System codes (HCPCS), and National Drug Codes (NDCs). Each of these standard healthcare codes undergoes modification every few years, and the techniques and system of the present description contemplate using any such version of each of the above-described codes. Other standard healthcare codes that may be included in patient healthcare data 118 may include Diagnostic Related Group (DRG) codes, and Enhanced Ambulatory Patient Group (EAPG) codes. In some examples, these DRG and EAPG codes may be determined from the other standard healthcare codes. Additionally, these DRG and EAPG codes may represent a specific category of disease or health problem the patient suffers from or has suffered from in the past.

In some particular examples, patient healthcare data 130 may include proprietary codes, such as All Patient Refined™ Diagnosis Related Groups (APR™ DRGs), available from 3M Company of Saint Paul, Minn. APR™ DRGs expand the basic DRG structure by adding two sets of subclasses to each base APR™ DRG. Each subclass set consists of four subclasses: one addresses patient differences relating to severity of illness and the other addresses differences in risk of mortality. Severity of illness is defined as the extent of physiologic decompensation or organ system loss of function. Risk of mortality is defined as the likelihood of dying. The additional data from APR™ DRGs as compared to the basic DRG structure may facilitate more accurate evaluations of the risks of future preventable patient healthcare events for a patient.

Different codes may be used with outpatient ancillary services as compared to inpatient services. Outpatient ancillary services represent auxiliary or supplemental services, such as diagnostic services, home health services, physical therapy and occupational therapy, used to support diagnosis and treatment of a patient's condition. In different examples, outpatient ancillary services may be characterized according to ambulatory patient group (APG) codes and/or according to enhanced ambulatory patient group (EAPG) codes, available from 3M Company of Saint Paul, Minn. APGs and EAPGs are to outpatient procedures what DRGs are to inpatient days; for example, EAPGs provide for a fixed reimbursement to an institution for outpatient procedures or visits and incorporate data regarding the reason for the visit and patient data.

Preventable event module 120 may further determine one or more patient factors based on patient healthcare data 130. Some examples of patient factors include a location of residence, the type of healthcare event, the sequence of events, and the clinical necessity for service.

In some examples, preventable event module 120 may determine the stage and severity of any diseases or other health problems based on patient healthcare data 130. For example, preventable event module 120 may use the one or more associated healthcare codes to determine the existence and severity of any disease or other health problem from which the patient suffers at the time of a healthcare event. These diseases and health problems may generally be referred to as comorbid diseases. For example, preventable event module 120 may determine comorbid diseases and severity based on one or more received healthcare codes associated with dates prior to the current event. In other words, preventable event module 120 may receive historical patient medical data, and from that data determine the stage and extent of any comorbid diseases. In some examples, the healthcare codes directly indicate the existence of any disease or other health problem and the severity level. In other examples, patient healthcare data 130 determines the existence of any disease or other health problem and severity level based on the treatment directly indicated by the one or more healthcare codes.

In some examples, as described previously, patient healthcare data 130 may include standard healthcare codes, such as ICD codes, CPT codes, HCPCS codes, and the like. At least some of these particular healthcare codes may be associated with future potentially preventable healthcare events or medical encounters. Accordingly, preventable event module 120 may use this historical data to produce a snapshot of the stage and extent of any comorbid disease a patient suffers from. As one example, preventable event module 120 may process the healthcare data to determine the existence and severity of any comorbid diseases in accordance with the techniques disclosed in U.S. Pat. No. 7,127,407 to Averill et al., the entire contents of which are incorporated by reference. For example, preventable event module 120 may categorize information included in patient healthcare data 130 into a multi-level categorical hierarchy.

As discussed in further detail below, preventable event module 120 may access patient healthcare data 130 and risk database 136, as well as, patient factors 132 and/or processed events 134 to evaluate future healthcare event risks of a patient. Preventable event module 120 may further present indications of the risks of potentially preventable healthcare events to a user via output device 116 to facilitate mitigation of the risks of potentially preventable healthcare events for the patient. For example, preventable event module 120 may further present indications of the risks of potentially preventable healthcare events to a user via a display of output device 116.

The system of FIG. 1 is a stand-alone system in which processor 112 that executed preventable event module 120 and output device 116 that outputs various data reside on the same computer 110. However, the techniques of this disclosure may also be performed in a distributed system that includes a server computer and a client computer. In this case, the client computer may communicate with the server computer via a network. The preventable event module may reside on the server computer, but the output device may reside on the client computer. In this case, when the preventable event module causes display prompts, the preventable event module causes the output device of the client computer to display the data, e.g., via commands or instructions communicated based on the server computer to the client computer.

Figure 2:
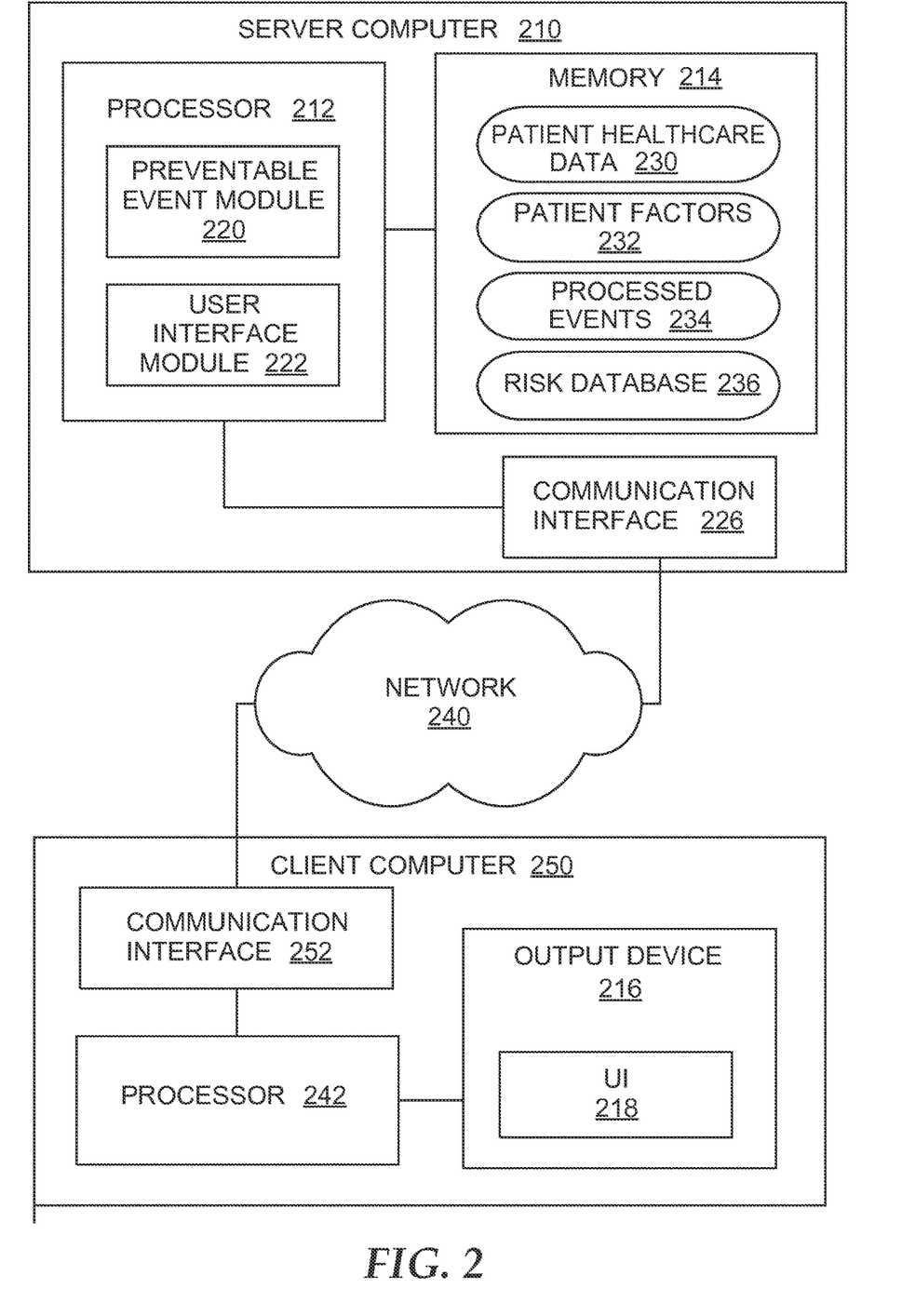
FIG. 2 is a block diagram illustrating an example of a distributed computer system for determining risks of potentially preventable healthcare events.

FIG. 2 is a block diagram of a distributed system that includes a server computer 210 and a client computer 250 that communicate via a network 240. In the example of FIG. 2, network 240 may comprise a proprietary on non-proprietary network for packet-based communication. In one example, network 240 comprises the Internet, in which case communication interfaces 226 and 252 may comprise interfaces for communicating data according to transmission control protocol/internet protocol (TCP/IP), user datagram protocol (UDP), or the like. More generally, however, network 240 may comprise any type of communication network, and may support wired communication, wireless communication, fiber optic communication, satellite communication, or any type of techniques for transferring data between a source (e.g., server computer 210) and a destination (e.g., client computer 250).

Server computer 210 may perform the techniques of this disclosure, but the user may interact with the system via client computer 250. Server computer 210 may include a processor 212, a memory 214, and a communication interface 226. Client computer 250 may include a communication interface 252, a processor 242 and an output device 216. Output device 216 may comprise a display screen, although this disclosure is not necessarily limited in this respect and other output devices may also be used. Of course, client computer 250 and server computer 210 may include many other components and the functions of any of the illustrated components, including server computer 210, processor 212, a memory 214, network 240, client computer 250, processor 242 and output device 216, may be distributed across multiple components and separate computing devices. The illustrated components are shown merely to explain various aspects of this disclosure.

Memory 214 stores patient healthcare data 230, which may comprise data collected in documents such as patient healthcare records, among other information. Memory 214 further includes risk database 236. Risk database 236 associates healthcare events and healthcare codes with risks of potentially preventable healthcare events. In some examples, risk database 236 includes a matrix or list that identifies potentially preventable healthcare events for each of a plurality of healthcare codes. Memory 214 may further stores patient factors 232 and/or processed events 234. Processor 212 of server computer 210 is configured to include preventable event module 220 that executes techniques of this disclosure with respect to patient healthcare data 230. Memory 214 may represent any volatile or non-volatile storage elements. Examples include random access memory (RAM) such as synchronous dynamic random access memory (SDRAM), read-only memory (ROM), non-volatile random access memory (NVRAM), electrically erasable programmable read-only memory (EEPROM), and FLASH memory. Examples may also include non-volatile storage, such as a hard-disk, magnetic tape, a magnetic or optical data storage media, a compact disk (CD), a digital versatile disk (DVD), a Blu-ray disk, and a holographic data storage media.

Processors 212 and 242 may each comprise a general-purpose microprocessor, a specially designed processor, an application specific integrated circuit (ASIC), a field programmable gate array (FPGA), a collection of discrete logic, or any type of processing device capable of executing the techniques described herein. In one example, memory 214 may store program instructions (e.g., software instructions) that are executed by processor 212 to carry out the techniques described herein. In other examples, the techniques may be executed by specifically programmed circuitry of processor 212. In these or other ways, processor 212 may be configured to execute the techniques described herein.

Output device 216 on client computer 250 may comprise a display screen, and may also include other types of output capabilities. For example, output device 216 may generally represent both a display screen and a printer in some cases. Preventable event module 220 may be configured to cause output device 216 of client computer 250 to output patient healthcare data 230 or processed events 234. User interface (UI) 218 may be generated, e.g., as output on a display screen, so as to allow a user enter various selection parameters or other information.

Similar to the standalone computer example of FIG. 1, in the distributed computing system example of FIG. 2, preventable event module 220 may determine risks of potentially preventable healthcare events based on patient healthcare data 230 and patient factors 232. Additionally, the other components of FIG. 2 with names similar to components depicted in FIG. 1 may perform similar functions as the components of FIG. 1 as described previously.

In some examples, preventable event module 220 may receive selection input from client computer 250. For example, preventable event module 220 may be configured to receive user input in order to determine the potentially preventable healthcare events. For example, a user may enter selection parameters at user interface (UI) 218. Again, communication interfaces 226 and 252 allow for communication between server computer 210 and client computer 250 via network 240. In this way, preventable event module 220 may execute on server computer 210, but may receive input from client computer 250. A user operating on client computer 250 may log-on or otherwise access preventable event module 220 of server computer 210, such as via a web-interface operating on the Internet or a propriety network, the Cloud, or via a direct or dial-up connection between client computer 250 and server computer 210. In some cases, data displayed on output device 230 may be arranged in web pages served from server computer 210 to client computer 250 via hypertext transfer protocol (HTTP), extended markup language (XML), or the like.

In at least one example, the user input may comprise parameters by which preventable event module 220 determines risks of potentially preventable healthcare events. A user may specify only certain patients for which to determine risks of potentially preventable healthcare events. In some examples, preventable event module 220 may be further configured to perform functions similar to preventable event module 120 as described in FIG. 1.

In at least one example, preventable event module 220 receives patient healthcare data 230. As described previously, patient healthcare data 230 may include information included in a patient healthcare record or any other documents or files describing a patient encounter with a healthcare facility, including medical claims forms. Patient healthcare data 230 may further include one or more standard healthcare codes, such as (ICD) codes (versions 9 and 10), Current Procedural Technology (CPT) codes, Healthcare Common Procedural Coding System codes (HCPCS), and Physician Quality Reporting System (PQRS) codes as described previously. Patient healthcare data 230 may also include other standard healthcare codes such as Diagnostic Related Group (DRG) codes and National Drug Codes (NDCs). These DRG codes may represent a specific category of disease or health problem the patient suffers from or has suffered from in the past if the DRG is associated with a past event.

Preventable event module 220 may then determine risks of potentially preventable healthcare events for individual patients. For example, preventable event module 220 may determine one or more healthcare events associated with one or more of the received healthcare codes. Preventable event module 220 may further determine one or more patient factors associated with the determined healthcare events. Preventable event module 220 may store these patient factors in memory 214 and/or patient factors 232.

According to techniques of the present disclosure, preventable event module 220 may then determine risks of potentially preventable healthcare events based on the one or more healthcare codes and the one or more determined patient factors and the associations between healthcare events and risks of potentially preventable healthcare events within risk database 236. Preventable event module 220 may determine these risks of potentially preventable healthcare events in accordance with the method described previously with respect to preventable event module 120.

Preventable event module 220 may then send, in some examples, in conjunction with user interface module 222, to communication interface 226, through network 240, to communication interface 252, to processor 242, and finally to output device 216. In this way, a user may view the results of the determination of potentially preventable healthcare events, and the risks of potentially preventable healthcare events may be mitigated.

Figure 3:
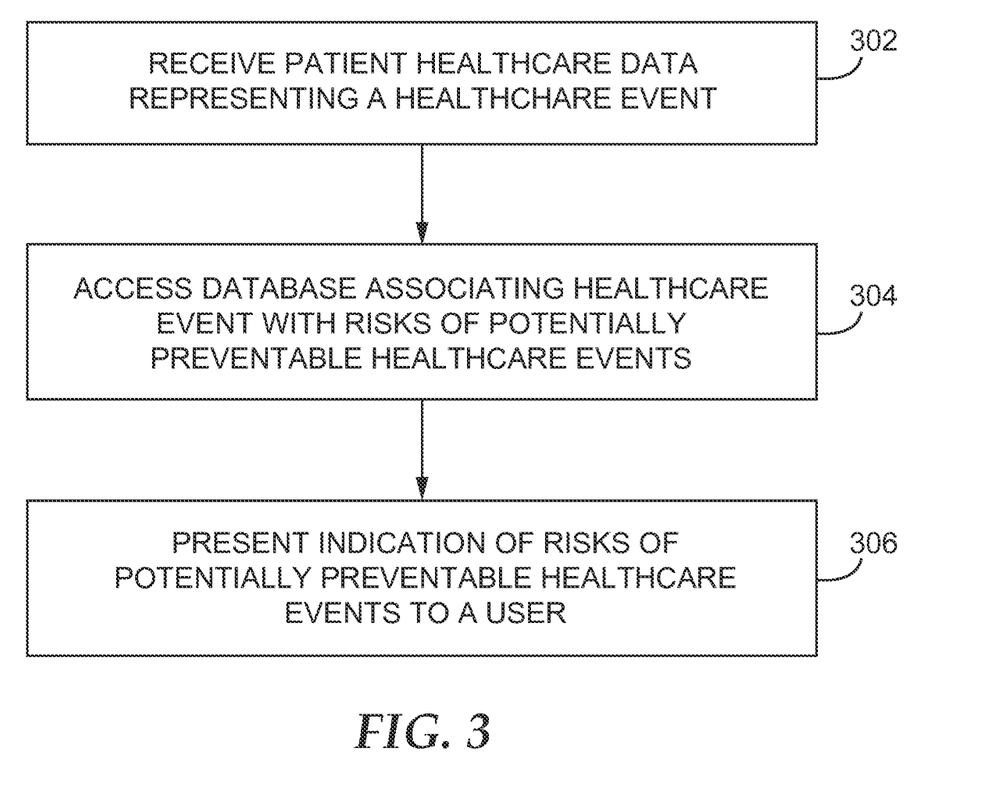
FIG. 3 is a flowchart illustrating an example technique for evaluating future healthcare event risks of a patient to facilitate mitigation of the risks of potentially preventable healthcare events for the patient.

FIG. 3 is a flowchart illustrating an example technique for evaluating future healthcare event risks of a patient to facilitate mitigation of the risks of potentially preventable healthcare events for the patient. For clarity, the techniques of FIG. 3 are described with respect to computer 110 of FIG. 1, although the techniques are equally applicable to a distributed computing system, including the example distributed computing system illustrated in FIG. 2.

Computer 110 receives patient healthcare data 130 for a patient (302). For example, computer 110 may receive patient healthcare data 130 from a patient from a remote database or computer 110 may maintain updated patient healthcare data 130 within memory 114. The patient healthcare data 130 represents a healthcare event and includes one or more healthcare codes. Computer 110 accesses risk database 136 (304). Risk database 136 associates a current healthcare event and the healthcare codes with risks of potentially preventable healthcare events. In some examples, risk database 136 includes a matrix or list that identifies potentially preventable healthcare events for each of a plurality of healthcare codes.

Computer 110 then presents indications of the risks of potentially preventable healthcare events to a user to facilitate mitigation of the risks of potentially preventable healthcare events for the patient via output device 116 (306). For example, computer 110 may present the relative probabilities of each of the potentially preventable healthcare events for the patient to the user. In some examples, presenting indications of the risks of potentially preventable healthcare events to the user includes selecting potentially preventable healthcare events with relatively higher risks among a plurality of potentially preventable healthcare events associated with the healthcare event and the healthcare codes in the database. In this manner, only the potentially preventable healthcare events with most severe risks may be displayed for a user, which may highlight these risks and improve the ability of the user to implement effective risk mitigation measures.

Figure 4:
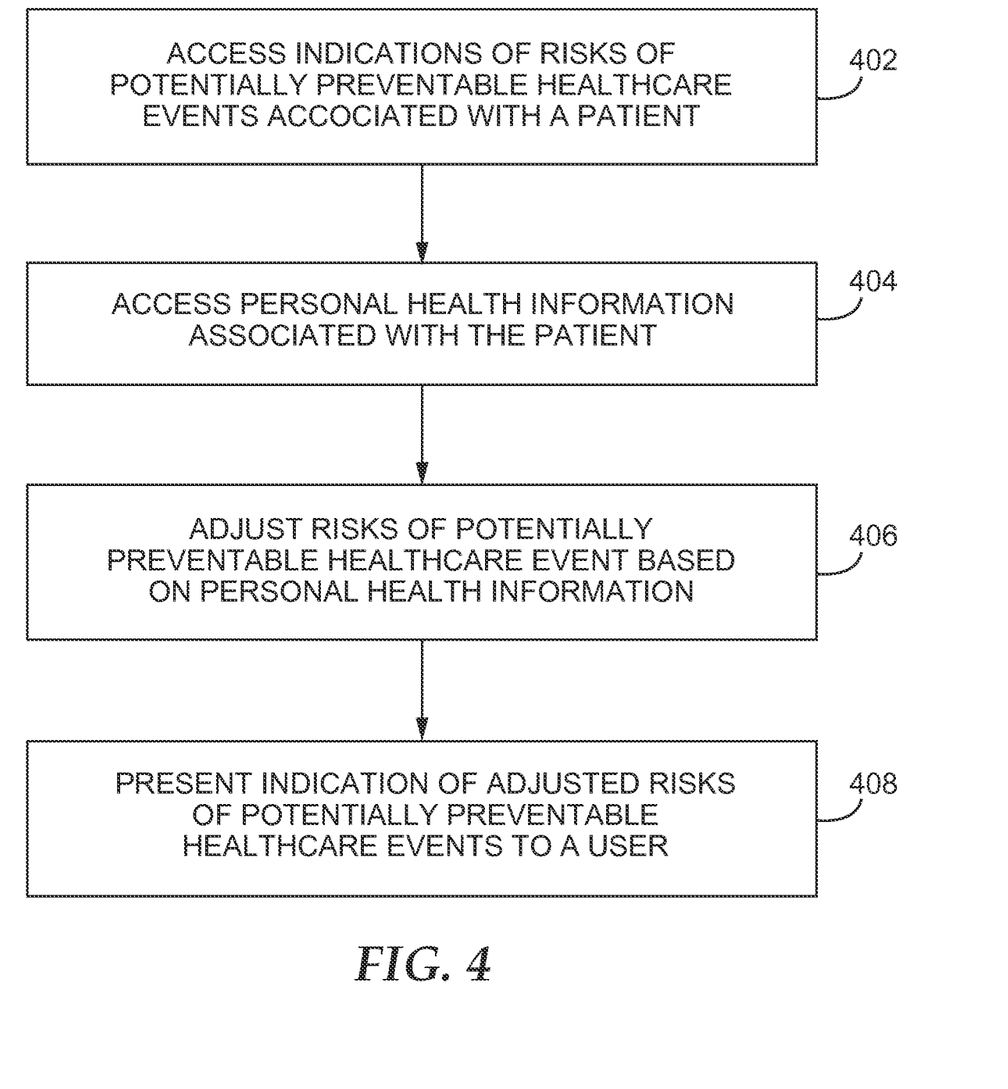
FIG. 4 is a flowchart illustrating an example technique for evaluating future healthcare event risks of a patient based on personal health information associated with the patient to facilitate mitigation of the risks of potentially preventable healthcare events for the patient.

In the same or different examples, as described in further detail with respect to FIG. 4, computer 110 may adjust the risks of potentially preventable healthcare events stored in risk database 136 based on personal health information associated with the patient, to produce adjusted risks of potentially preventable healthcare events. In this manner, the baseline risks of potentially preventable healthcare events stored within risk database may be adjusted to more accurately characterize the risks of potentially preventable healthcare events for an individual patient based on personal health information associated with the patient. In such examples, presenting the indications of the risks of potentially preventable healthcare events to the user may include presenting indications of the adjusted risks of potentially preventable healthcare events to the user.

In some examples, computer 110 may create or update associations between healthcare events and healthcare codes within risk database 136. As one example, computer 110 may access a database of healthcare data for a plurality of patients in order to find correlations between healthcare events within the healthcare data. Computer 110 may further determine the probability of potentially preventable healthcare events for each healthcare code within the database. In one particular example, computer 110 may create or update associations between healthcare events and healthcare codes within risk database 136 using administrative claims data. Administrative claims data may include DRG codes, or APR™-DRG codes for a large group of patients.

In addition, with respect to a particular healthcare event, or event category, computer 110 may limit statistical analysis of healthcare codes to healthcare events that have been classified as being potentially preventable healthcare events of that particular event. In some particular examples, the Potentially Preventable Readmissions Classification System (PPR), available from 3M Company of Saint Paul, Minn. may be used as the basis for determining which healthcare events are classified as being potentially preventable healthcare events of that particular event.

In summary, computer 110 may update the probability of potentially preventable healthcare events (the list of potentially preventable healthcare events being preclassified as being potentially preventable healthcare events by PPR or otherwise) for each possible healthcare event code, such as APR™ DRG code, according to a broad healthcare database, such as an administrative claims database. The updated probabilities based on the analysis of the broad healthcare database may then be stored in a probability matrix for use to evaluate the risks of all possible potentially preventable healthcare events for a patient based on the patient's current healthcare event. In this manner, the probability matrix only includes probabilities of potential future healthcare events that are preclassified as being potentially preventable. Probabilities of potential future healthcare events that are not related to a particular healthcare event being analyzed are excluded from the matrix. For example, while a patient who had coronary bypass surgery may later experience an appendicitis or be injured in a car accident, these potential healthcare events are not potentially preventable as they are unrelated to the coronary bypass surgery. For this reason, the matrix would not include the probabilities of an appendicitis or car accident injuries with respect to the healthcare event of coronary bypass surgery. In contrast, the matrix would include the probability of post-surgical infection as a post-surgical infection may be related to coronary bypass surgery, and therefore is considered potentially preventable.

In the same or different examples, the probability matrix may further incorporate severity factors of potentially preventable healthcare events. The severity factors may include a clinical severity of the potentially preventable healthcare event, a financial severity of the potentially preventable healthcare event and/or other severity metric beyond the simple probability of the classified potentially preventable healthcare events. The severity factors may be incorporated into the probability matrix to create a risk matrix in which includes a risk factor for all classified preventable healthcare events. In other examples, the risk factors in the risk matrix may simply represent the probabilities of each of the potentially preventable healthcare events. Thus, as referred to herein, the risk factors in the risk matrix may represent any combination of factors in conjunction with a simple risk probability, including, but not limited to, a financial risk based on the relative probability of possible readmission outcomes and their costs, and/or represent clinical severity in order to limit acute outcomes, like death.

In this manner, computer 110 may, for each of the plurality of healthcare codes, calculates a risk factor for each of the potentially preventable healthcare events identified with that healthcare code based on the administrative claims data. For each of the plurality of healthcare codes, computer 110 may then store the risk factor for each of the potentially preventable healthcare events identified with that healthcare code in risk database 136 to associate the healthcare codes with risks of potentially preventable healthcare events.

FIG. 4 is a flowchart illustrating an example technique for evaluating future healthcare event risks of a patient based on the personal health information associated with the patient to facilitate mitigation of the risks of potentially preventable healthcare events for the patient. The techniques of FIG. 4 facilitate adjustment of the baseline risks of potentially preventable healthcare events stored in risk database 136 based on personal health information associated with a patient, to produce adjusted risks of potentially preventable healthcare events for an individual patient. As referred to herein, the baseline risks of potentially preventable healthcare events associated with a patient are based simply on a singular healthcare event of the patient, and not based on further patient-specific information. For example, the baseline risks of potentially preventable healthcare events associated with a patient may be determined solely based on coding of the single health event, such as DRG coding and/or APR™ DRGs coding.

While the techniques of FIG. 4 may be used to improve the accuracy of the indications of the baseline risks of potentially preventable healthcare events described with respect to FIG. 3, the techniques of FIG. 4 may also be utilized to improve the accuracy of risk calculations of potentially preventable healthcare events determined in any manner. For clarity, the techniques of FIG. 4 are described with respect to computer 110 of FIG. 1, although the techniques are equally applicable to a distributed computing system, including the example distributed computing system illustrated in FIG. 2.

Computer 110 accesses indications of risks of potentially preventable healthcare events associated with a patient (402). For example, computer 110, including processor 112, may perform the techniques for determining risks of potentially preventable healthcare events associated with a patient as described with respect to FIG. 3. In some particular examples, processor 112 receives an indication of a healthcare event of a patient, such as an event recorded in patient healthcare data 130 and accesses indications of risks of potentially preventable healthcare events associated with the event, e.g., via a probability matrix or risk matrix within risk database 136.

No matter how processor 112 accesses indications of risks of potentially preventable healthcare events associated with a patient, processor 112 also accesses personal health information associated with the patient (404). The personal health information associated with the patient may be located within patient healthcare data 130. The personal health information associated with the patient may be located within patient healthcare data 130. As one example, the patient's chronic disease burden and health status may have a significant effect upon the residual probability of occurrence of specific types of readmissions. In one particular example, the 3M Clinical Risk Groups (CRG) tool, available from 3M Company of Saint Paul, Minn., may be used to define a patient's chronic disease burden and health status.

As one example, the personal health information may include records of prior healthcare events of the patient, and such records are commonly available as prior claims data. As other examples, the personal health information may include electronic health records for the patient with structured and/or unstructured data. Computer 110 may analyze unstructured data using natural language processing techniques in order to find personal health information relevant to the adjusting the determined baseline risks of potentially preventable healthcare events associated with a patient. As one example, computer-based techniques for searching and identifying key clinical concepts within medical documents using natural language processing (NLP) for searching and identify key clinical concepts within medical documents are disclosed in U.S. Pat. Application No. 61/771,573 filed Mar. 1, 2013, titled IDENTIFICATION OF CLINICAL CONCEPTS FROM MEDICAL RECORDS, the entire contents of which are incorporated by reference herein.

Processor 112 then adjusts the risks of potentially preventable healthcare events associated with the patient based on the personal health information associated with the patient, to produce adjusted risks of potentially preventable healthcare events (406). Thus, whereas the baseline risks of potentially preventable healthcare events associated with the patient merely accounted for a singular health event of the patient, the adjusted risks of potentially preventable healthcare events incorporate personal health information of the patient into the determination of the risks of potentially preventable healthcare events associated with the patient.

In some examples, processor 112 may incorporate additional patient-specific information to determine the adjusted risks of potentially preventable healthcare events associated with the patient. For example, processor 112 may access demographic information about the patient. Processor 112 may determine the adjusted risks of potentially preventable healthcare events associated with the patient further based on the demographic information. In some examples, such demographic information may include one or more of gender, age, income, ethnicity, housing status, home address, employment status, and marital status.

As another example, computer 110 may request a user provide personal information about the patient and receive the requested personal information about the patient in response to the request via user interface 122. As one example, if personal information available to processor 112 is incomplete in order to perform an adequate determination of the adjusted risks of potentially preventable healthcare events associated with the patient, processor 112 may request the missing information from a user, such as a clinician or the patient. Processor 112 may then determine the adjusted risks of potentially preventable healthcare events associated with the patient further based on the personal information received via the user interface.

Computer 110 presents indications of the adjusted risks of potentially preventable healthcare events to a user to facilitate mitigation of the risks of potentially preventable healthcare events for the patient (408). For example, computer 110 may present the relative probabilities of each of the potentially preventable healthcare events for the patient to the user. In some examples, presenting indications of the adjusted risks of potentially preventable healthcare events to the user includes selecting potentially preventable healthcare events with relatively higher adjusted risks among a plurality of potentially preventable healthcare events associated with the healthcare event and the healthcare codes in the database and presenting indications of the selected potentially preventable healthcare events with relatively higher adjusted risks to the user. In this manner, only the potentially preventable healthcare events with most severe adjusted risks may be displayed for a user, which may highlight these risks and improve the ability of the user to implement effective risk mitigation measures.

As described with respect to FIG. 3, computer 110, including processor 112, may create or update associations between healthcare events and healthcare codes within risk database 136 by accessing a database of healthcare data for a plurality of patients computer 110 and evaluating the probability of potentially preventable healthcare events, the list of potentially preventable healthcare events being pre-classified as being potentially preventable healthcare events. Similar techniques may be applied to determine adjustment factors to the baseline risks of potentially preventable healthcare events associated with a patient based on personal patient health information, including prior medical event information, demographic information and/or other personal information. Alternately or in addition to using statistical analysis to determine adjustment factors to the baseline risks of potentially preventable healthcare events associated with a patient based on personal patient information expert consensus, e.g., based on published studies may be used to determine adjustment factors to the baseline risks of potentially preventable healthcare events associated with a patient based on personal patient information. For example, it is widely understood that homeless patients have much higher readmission rates. However, the housing status of patients may not be generally available in large volumes of patient records, such as administrative claims data. Accordingly, even though the housing status of patients may have a significant impact on the actual risks of potentially preventable healthcare events associated with a patient, there may not be sufficient patient records to determine appropriate adjustment factors to the baseline risks using only statistical analysis. In this example, using expert consensus may allow for more accurate determinations of risks of potentially preventable healthcare events associated with a patient than allowed by statistical analysis alone. In further examples, a combination of expert consensus and statistical information may be used to determine adjustment factors based on personal patient information.

Figure 5:
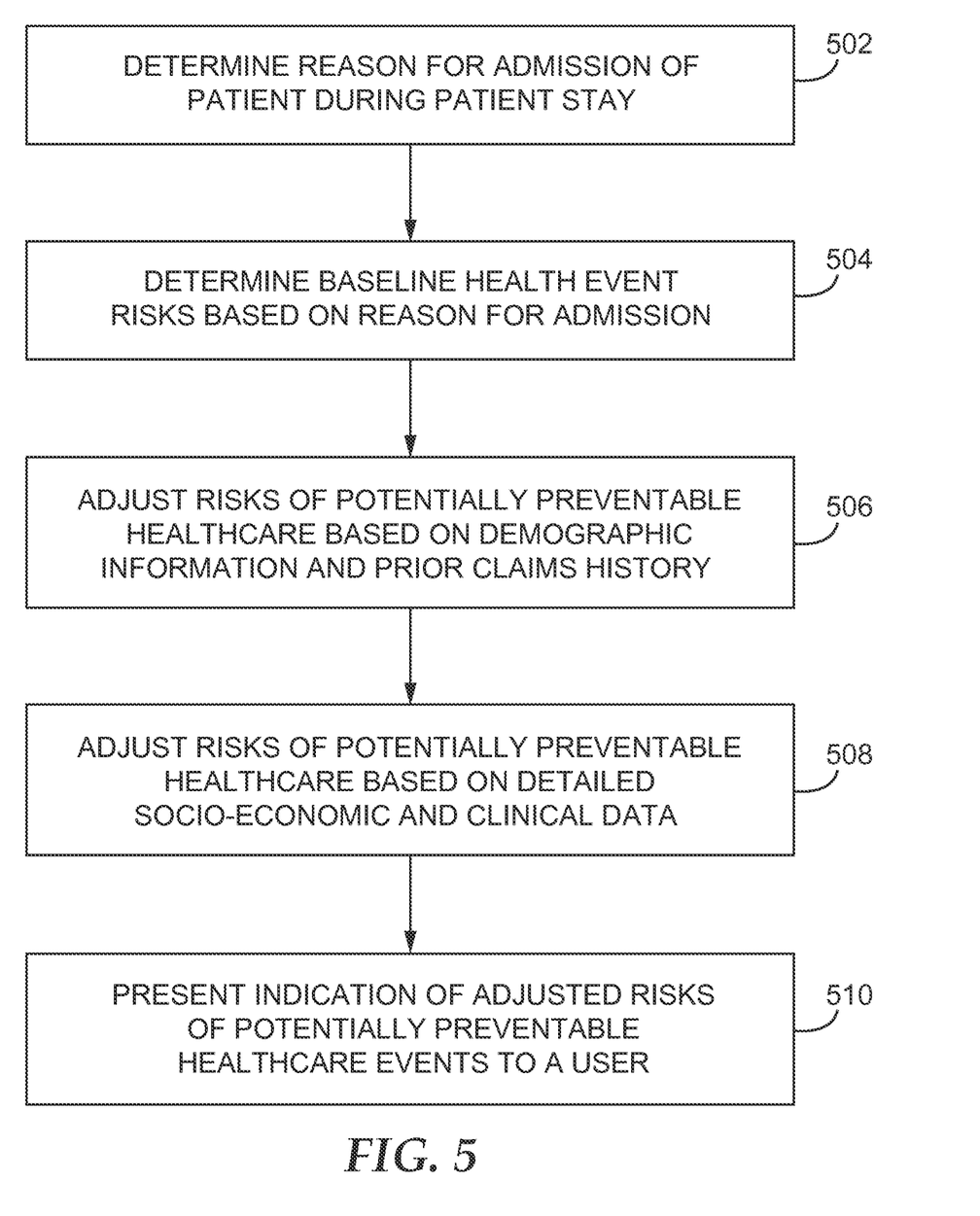
FIG. 5 is a flowchart illustrating an example technique for evaluating future healthcare event risks of a patient based on personal information associated with the patient to facilitate mitigation of the risks of potentially preventable healthcare events for the patient.

FIG. 5 is a flowchart illustrating an example technique for evaluating future healthcare event risks of a patient based on personal information associated with the patient to facilitate mitigation of the risks of potentially preventable healthcare events for the patient.

The techniques of FIG. 5 facilitate adjustment of the baseline risks of potentially preventable healthcare events stored in risk database 136 based on personal health information associated with a patient, to produce adjusted risks of potentially preventable healthcare events for an individual patient. For example, the baseline risks of potentially preventable healthcare events associated with a patient may be determined solely based on coding of the single health event, such as DRG coding and/or APR™ DRGs coding.

While the techniques of FIG. 5 may be used to improve the accuracy of the indications of the baseline risks of potentially preventable healthcare events described with respect to FIG. 3, the techniques of FIG. 5 may also be utilized to improve the accuracy of risk calculations of potentially preventable healthcare events determined in any manner. For clarity, the techniques of FIG. 5 are described with respect to computer 110 of FIG. 1, although the techniques are equally applicable to a distributed computing system, including the example distributed computing system illustrated in FIG. 2.

The techniques of FIG. 5 incorporate a three stage predictive model with each subsequent stage refining the prior assessment of the probability of specific types of potentially preventable healthcare events so as to better account for an individual patient's risks of potentially preventable healthcare events. The techniques of FIG. 5 may incorporate a mathematical model that is structurally similar to a three stage least squares (3SLS) model that uses a single iteration to compute baseline probability of a potentially preventable healthcare event before layering in additional variables to explain residual variation and improve the prediction of the probability of a potentially preventable healthcare event, such as a hospital readmission event. In some examples, the techniques of FIG. 5 are limited to predicting the probabilities of potentially preventable hospital readmissions or predicting the probabilities potentially preventable hospital readmissions, ER stays and outpatient observation stays.

The first two stages (steps 502, 504 and 506) utilize routinely collected administrative data that includes principal and secondary diagnoses, procedures, procedure dates, age and sex. The third stage (steps 508) utilizes data from an electronic health record or data collected as an independent adjunct to the administrative data that includes socioeconomic status (e.g., living alone), functional status (e.g., ability to ambulate), pharmaceutical usage and detailed clinical data such as history and physical and laboratory test results. In stage one, only data from a current medical event of the patient is used. In stages two and three, data from the patient's medical history prior to medical event is used if available.

In stage one, computer 110 uses administrative claims data to classify a patient based on his or her current medical event, such as a reason for hospital admission, using a mutually exclusive and exhaustive set of reasons for hospitalization, such as APR™ DRGs (502). In APR™ DRGs the acuity (severity of illness) of the patient is assign based on a four-category scale: minor, moderate, major, or extreme. Each combination of a current healthcare event, a potential future healthcare event and acuity form a unique category.

Based on the identified current healthcare event, all possible potentially preventable reasons for healthcare event are identified, for example, based on PPR. Using large historical databases the rate of (probability of) specific potentially preventable healthcare events has been computed for each unique combination of reason for admission and acuity (referred to as the baseline readmission probability matrix). In stage one, based on a patient's reason for admission and acuity, the baseline probability of specific types of potentially preventable healthcare event is determined by looking up the baseline probability in the baseline healthcare event probability matrix (504). Thus, stage one (steps 502 and 504) is generally similar, and may indeed be the same as the techniques described with respect to FIG. 3.

In the second stage, computer 110 adjusts the baseline probability of specific types of healthcare events by computing the impact of demographics and the patient's chronic disease burden and health status upon the residual probability of occurrence of specific types of healthcare events (506). In one particular example, the 3M CRG tool may be used to define a patient's chronic disease burden and health status. In addition, computer 110 may determine a more accurate assessment of a patient's chronic disease burden and health status if a patient's claims history is available for the period preceding the current medical event because computer 110 may determine of the time of onset, frequency and recency of treatment of disease. When the prior claims history is available, computer 110 may incorporate the prior claims history in stage two to compute chronic disease burden and health status.

Using large historical databases for each reason for admission, the impact of demographics and the patient's chronic disease burden and health status upon the baseline probability of occurrence of specific types of healthcare events has been computed (referred to as the baseline adjustment factor matrix). In stage two, based on a patient's reason for admission, demographic, chronic disease burden and health status, computer 110 determines the adjustment factors for specific types of potentially preventable healthcare event by looking up the adjustment factors in the baseline adjustment factor matrix. Since prior claims history data may not always be available, the baseline adjustment factor matrix may contain two set of factors based on whether prior claims history was available for use in determining chronic illness burden and health status. Thus, stage two (step 506) represents one example, of the techniques described with respect to FIG. 4.

Likewise, stage three (step 508) represents a further refinement of the determined risks of potentially preventable healthcare events of a patient. For this reason, stage three represents another example of the techniques described with respect to FIG. 4. In the third stage, computer 110 further adjusts the probability of specific types of potentially preventable healthcare events from stage two by incorporating the impact of detailed personal information (508). Such detailed personal information may include socioeconomic status (e.g., living alone), functional status (e.g., ability to ambulate), pharmaceutical usage and detailed clinical data such as history and physical, laboratory test results, temperature on discharge, and positive blood cultures. In some examples, computer 110 may obtain detailed socio-economic and clinical data from an electronic health record (if available) or by direct data entry by hospital staff using a structured data collection instrument that is dynamically tailored to the patient based on his/her reason for admission. Using large historical databases for each reason for admission, the impact of detailed socio-economic and clinical data upon the stage two probability of occurrence of specific types of healthcare events has been computed (referred in this example as the clinical adjustment factor matrix). If there are socio-economic or clinical data that is not contained in any large historical databases but that the published literature has shown have an impact on the probability of a healthcare event, the published literature may be used as a basis for the clinical adjustment factor matrix. For example, clinical consensus panels may be used to establish the stage three adjustment factors for these variables. In stage three, based on a patient's detailed socio-economic and clinical data the adjustment factors for specific types of potentially preventable healthcare event is determined by looking up the adjustment factors in the clinical adjustment factor matrix.

Computer 110 presents indications of the adjusted risks of potentially preventable healthcare events to a user to facilitate mitigation of the risks of potentially preventable healthcare events for the patient via output device 116 (510). For example, computer 110 may present the relative probabilities of each of the potentially preventable healthcare events for the patient to the user. In some examples, presenting indications of the adjusted risks of potentially preventable healthcare events to the user includes selecting potentially preventable healthcare events with relatively higher adjusted risks among a plurality of potentially preventable healthcare events associated with the healthcare event and the healthcare codes in the database. In this manner, only the potentially preventable healthcare events with most severe adjusted risks may be displayed for a user, which may highlight these risks and improve the ability of the user to implement effective risk mitigation measures.

The result of this three stage predictive model is a computed probability that a patient will have a potentially preventable healthcare event with a specification of the likely reasons for the healthcare event. For example, the three stage predictive model may indicate for a single patient: a twenty percent chance of a preventable healthcare event with fifty percent of those healthcare events being for a post-operative wound infection, thirty percent being for a reoccurrence of the original reason for admission, and twenty percent being for other reasons. The probability can be used directly or converted into low to high scale depending on the preference of the user.

In some particular examples, the techniques of FIG. 5, as well as the techniques of FIG. 3 and FIG. 4, as described above, may be specifically directed to determining risks of potentially preventable readmissions. In further more specific examples, such techniques may be applied to determining risks of potentially preventable hospital readmissions only or risks of potentially preventable hospital readmissions, ER stays and outpatient observation stays. In such specific examples, two different baseline risk matrixes may be used: one for determining risks of potentially preventable hospital readmissions only and another for determining the total risks of potentially preventable hospital readmissions, extended ER visits and outpatient observation stays.

Because extended ER visits or observation stays can substitute for a hospital admission, all the probabilities and adjustment factors in the baseline healthcare event probability matrix, the baseline adjustment factor matrix, and the clinical adjustment factor matrix are also recomputed with extended ER visits or observation stays treated as if they were a hospital admission. By treating an extended ER visit or observation stay as if it were a hospital admission, the probability computed by the model represents the probability of a potentially preventable hospital readmission or a potentially preventable subsequent ER visit or observation stay. In some examples, a provider, such as a hospital, can select which probability it prefers the model to compute. In different examples, both probabilities may be presented to a user.

By utilizing a three stage predictive model that establishes a clinically based (reason for admission and acuity) baseline probability of specific types of potentially preventable healthcare event prior to adjusting the probability based on other factors, a greater independence of the prediction from the specific data used to compute the probabilities is achieved. This model minimizes the cross correlation of complex clinical factors and non-clinical factors avoiding the variance inflation observed by other models.

The techniques of this disclosure may be implemented in a wide variety of computer devices, such as servers (including the Cloud), laptop computers, desktop computers, notebook computers, tablet computers, hand-held computers, smart phones, and the like. Any components, modules or units have been described to emphasize functional aspects and does not necessarily require realization by different hardware units. The techniques described herein may also be implemented in hardware, software, firmware, or any combination thereof. Any features described as modules, units or components may be implemented together in an integrated logic device or separately as discrete but interoperable logic devices. In some cases, various features may be implemented as an integrated circuit device, such as an integrated circuit chip or chipset. Additionally, although a number of distinct modules have been described throughout this description, many of which perform unique functions, all the functions of all of the modules may be combined into a single module, or even split into further additional modules. The modules described herein are only exemplary and have been described as such for better ease of understanding.

If implemented in software, the techniques may be realized at least in part by a computer-readable medium comprising instructions that, when executed in a processor, performs one or more of the methods described above. The computer-readable medium may comprise a tangible computer-readable storage medium and may form part of a computer program product, which may include packaging materials. The computer-readable storage medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The computer-readable storage medium may also comprise a non-volatile storage device, such as a hard-disk, magnetic tape, a compact disk (CD), digital versatile disk (DVD), Blu-ray disk, holographic data storage media, or other non-volatile storage device.

The term "processor," as used herein may refer to any of the foregoing structure or any other structure suitable for implementation of the techniques described herein. In addition, in some aspects, the functionality described herein may be provided within dedicated software modules or hardware modules configured for performing the techniques of this disclosure. Even if implemented in software, the techniques may use hardware such as a processor to execute the software, and a memory to store the software. In any such cases, the computers described herein may define a specific machine that is capable of executing the specific functions described herein. Also, the techniques could be fully implemented in one or more circuits or logic elements, which could also be considered a processor.

Various examples have been described. For example, while the techniques disclosed herein have generally included evaluating future healthcare event risks of a single patient, the technique may also be applied to evaluating future healthcare event risks of multiple patients, such that the relative future healthcare event risks of each patient of a group of patients may be compared. For example, by presenting the relative future healthcare event risks of each patient of a group of patients within a medical facility, the medical facility may then use such information to allocate resources to mitigate the future healthcare event risks of its patients most efficiently. In this manner, the techniques disclosed herein may have particular applicability to improving patient care management for a medical facility or other medical care provider. These and other examples are within the scope of the following claims.

What is claimed is:

1. A method of generating a model for evaluating future healthcare event risks of a patient, via one or more computers, the method comprising:
   receiving, at a memory of one or more computers communicatively coupled over a network, patient healthcare data for the patient, wherein the patient healthcare data represents a current healthcare event and includes one or more healthcare codes associated with the current healthcare event;
   storing, in the memory, the patient healthcare data;
   accessing, with the one or more computers, a database that associates the current healthcare event and the healthcare codes with risks of potentially preventable healthcare events, wherein the potentially preventable healthcare events are potentially preventable hospital readmissions;
   determining, with the one or more computers, one or more initial risk probabilities of potentially preventable healthcare events associated with the patient based on the association of the current healthcare event and the healthcare codes with risks of potentially preventable healthcare events;
   generating, with the one or more computers, an initial predictive multi-level categorical model that comprises the one or more determined initial risk probabilities and wherein potential future healthcare events that are not related to the current healthcare event are excluded from the initial predictive multi-level categorical model based on the associations contained in the database;
   accessing, with the one or more computers, personal information stored in the memory of the one or more computers and associated with the patient and demographic information about the patient;
   successively refining, with the one or more computers, the one or more initial risk probabilities of potentially preventable healthcare events in the initial predictive multi-level categorical model associated with the patient, wherein a first refinement includes determining, by the one or more computers, an impact of the demographics of the patient and the patient's health status upon the probability of an occurrence of one or more specific types of healthcare events to determine one or more first refined risk probabilities and a second refinement includes determining, by the one or more computers, an impact of the personal information of the patient upon the one or more first refined risk probabilities to determine one or more second refined risk probabilities, wherein refining the one or more initial risk probabilities improves the accuracy of the predictive categorical model resulting in an improved predictive categorical model; and
   storing the improved predictive categorical model by at least modifying information contained in the database that associates the current healthcare event and the healthcare codes with risks of potentially preventable healthcare events based on the one or more determined second refined risk probabilities.

2. The method of claim 1, wherein the demographic information includes at least one of a group consisting of:

gender;
age;
income;
ethnicity;
housing status;
home address;
employment status; and
marital status.

3. The method of claim 1, further comprising:
storing the improved categorical model on the database;
accessing the improved categorical model on the database that identifies potentially preventable healthcare events for each of a plurality of healthcare codes;
accessing administrative claims data to classify the current medical event of the patient;
for each of the plurality of healthcare codes, calculating a risk factor for each of the potentially preventable healthcare events identified with that healthcare code based on the administrative claims data; and
for each of the plurality of healthcare codes, storing the risk factor for each of the potentially preventable healthcare events identified with that healthcare code in the database to associate the healthcare codes with the risks of potentially preventable healthcare events.

4. The method of claim 1, wherein the healthcare event includes at least one of a group consisting of:
an inpatient admission;
an emergency room visit; and
an outpatient ancillary service.

5. The method of claim 1, further comprising:
generating data, by at least one of the one or more computers, that when received by the one or more computers causes the one or more computers to display information comprising the one or more second refined risk probabilities of potentially preventable healthcare events to be displayed on an output device of the one or more computers; and
transmitting the generated data to the one or more computers causing indications of the one or more second refined risk probabilities of potentially preventable healthcare events to be displayed on the one or more computers,
wherein generating data that when received by the one or more computers causes the one or more computers to display information comprising the one or more second refined risk probabilities of potentially preventable healthcare events to be displayed on an output device of the one or more computers includes selecting potentially preventable healthcare events with relatively higher risks among a plurality of potentially preventable healthcare events associated with the current healthcare event and the healthcare codes in the database and the generated data causes indications of the selected potentially preventable healthcare events with relatively higher risks to be displayed on the one or more computers.

6. The method of claim 1, wherein the indications of the risks of potentially preventable healthcare events includes an indication, for each of the potentially preventable healthcare events, of one or more of a group consisting of:
a probability of the potentially preventable healthcare event;
a clinical severity of the potentially preventable healthcare event;
a financial severity of the potentially preventable healthcare event; and
a compilation of at least two of: the probability of the potentially preventable healthcare event, the clinical severity of the potentially preventable healthcare event, and the financial severity of the potentially preventable healthcare event.

7. A computer system comprising:
a client computer configured to output patient healthcare data to one or more databases;
a computer readable storage medium including one or more databases stored thereon and configured to store patient healthcare data for a patient and associations between healthcare codes and risks of potentially preventable healthcare events; and
a server computer, comprising:
a network interface configured to enable the server computer to communicate with the client computer;
one or more computer processors configured to:
access the patient healthcare data for the patient, wherein the patient healthcare data represents a current healthcare event and includes one or more healthcare codes associated with the current healthcare event;
access a database that associates the current healthcare event and the healthcare codes with risks of potentially preventable healthcare events, wherein the potentially preventable healthcare events are potentially preventable hospital readmissions;
determine one or more initial risk probabilities of potentially preventable healthcare events associated with the patient based on the association of the current healthcare event and the healthcare codes with risks of potentially preventable healthcare events;
generate an initial predictive multi-level categorical model that comprises the one or more determined initial risk probabilities and wherein potential future healthcare events that are not related to the current healthcare event are excluded from the initial predictive multi-level categorical model based on the associations contained in the database;
access personal information stored in the memory of the one or more computers and associated with the patient and demographic information about the patient;
successively refine the one or more initial risk probabilities of potentially preventable healthcare events in the initial predictive multi-level categorical model associated with the patient, wherein a first refinement includes determining an impact of the demographics of the patient and the patient's health status upon the probability of an occurrence of one or more specific types of healthcare events to determine one or more first refined risk probabilities and a second refinement includes determining an impact of the personal information of the patient upon the one or more first refined risk probabilities to determine one or more second refined risk probabilities, wherein refining the one or more initial risk probabilities improves the accuracy of the predictive categorical model resulting in an improved predictive categorical model; and
store the improved predictive categorical model by at least modifying information contained in the database that associates the current healthcare event and the healthcare codes with risks of potentially preventable healthcare events based on the one or more second refined risk probabilities.

8. The computer system of claim 7, wherein the healthcare event includes at least one of a group consisting of:
- an inpatient admission;
- an emergency room visit; and
- an outpatient ancillary service.

9. The computer system of claim 7, wherein the potentially preventable healthcare events are potentially preventable hospital readmissions.

10. The computer system of claim 7, wherein the database stores only the associations between healthcare codes and risks of potentially preventable healthcare events and does not store risks of potential healthcare events not associated with a particular healthcare code.

11. A method of generating a model for evaluating future readmission risks of a patient, via one or more computers, the method comprising:
- receiving, at a memory of one or more computers communicatively coupled over a network, patient healthcare data for the patient, wherein the patient healthcare data represents a current healthcare event associated with a hospital admission and includes one or more healthcare codes associated with the current healthcare event;
- storing, in the memory, the patient healthcare data;
- accessing, with the one or more computers, a database that associates the healthcare codes with risks of potentially preventable readmission events;
- determining, with the one or more computers, one or more initial risk probabilities of potentially preventable readmission events associated with the patient based on the association of the current healthcare event and the healthcare codes with risks of potentially preventable readmission events;
- generating, with the one or more computers, an initial predictive multi-level categorical model that comprises the one or more determined initial risk probabilities and wherein potential future healthcare events that are not related to the current healthcare event are excluded from the initial predictive multi-level categorical model based on the associations contained in the database;
- accessing, with the one or more computers, personal information stored in the memory of the one or more computers and associated with the patient and demographic information about the patient;
- successively refining, with the one or more computers, the one or more initial risk probabilities of potentially preventable healthcare events in the initial predictive multi-level categorical model associated with the patient, wherein a first refinement includes determining, by the one or more computers, an impact of the demographics of the patient and the patient's health status upon the probability of an occurrence of one or more specific types of healthcare events to determine one or more first refined risk probabilities and a second refinement includes determining, by the one or more computers, an impact of the personal information of the patient upon the one or more first refined risk probabilities to determine one or more second refined risk probabilities, wherein refining the one or more initial risk probabilities improves the accuracy of the predictive categorical model resulting in an improved predictive categorical model; and
- storing the improved predictive categorical model by at least modifying information contained in the database that associates the current healthcare event and the healthcare codes with risks of potentially preventable healthcare events based on the one or more determined second refined risk probabilities.

12. The method of claim 11, wherein the readmission events consists of hospital readmission events.

13. The method of claim 11, wherein the readmission events consist of hospital readmission events, emergency room visits, and observation stays.

14. The method of claim 1, wherein the detailed personal information is selected from the group consisting of: socioeconomic status, functional status, pharmaceutical usage and detailed clinical data such as history and physical, laboratory test results, temperature on discharge, and positive blood cultures.

15. The method of claim 11, wherein the first refinement further comprises:
- determining a reason for admission of the patient during the patient stay based on the patient healthcare data;
- determining an impact of the reason for admission upon the probability of an occurrence of one or more specific types of healthcare events; and
- the determined first refined risk probabilities are further adjusted based on the determined impact.

16. The method of claim 1, wherein the first refinement further comprises:
- determining a reason for admission of the patient during the patient stay based on the patient healthcare data; and
- determining an impact of the reason for admission upon the probability of an occurrence of one or more specific types of healthcare events; and
- the determined first refined risk probabilities are further adjusted based on the determined impact.

17. The system of claim 7, wherein the first refinement further comprises:
- determining a reason for admission of the patient during the patient stay based on the patient healthcare data; and
- determining an impact of the reason for admission upon the probability of an occurrence of one or more specific types of healthcare events; and
- the determined first refined risk probabilities are further adjusted based on the determined impact.

18. The method of claim 1, wherein the first refinement further includes determining, by the one or more computers, an impact of the demographics of the patient and the patient's chronic disease burden upon the probability of an occurrence of one or more specific types of healthcare events to determine one or more first refined risk probabilities.

19. The system of claim 7, wherein the first refinement further includes determining, by the one or more computers, an impact of the demographics of the patient and the patient's chronic disease burden upon the probability of an occurrence of one or more specific types of healthcare events to determine one or more first refined risk probabilities.

20. The method of claim 11, wherein the first refinement further includes determining, by the one or more computers, an impact of the demographics of the patient and the patient's chronic disease burden upon the probability of an occurrence of one or more specific types of healthcare events to determine one or more first refined risk probabilities.

* * * * *